(12) United States Patent
Matsui et al.

(10) Patent No.: US 9,151,759 B2
(45) Date of Patent: Oct. 6, 2015

(54) METHOD FOR DETECTING CELLS WITH ELASTIC CELL MEMBRANES

(71) Applicant: Research Foundation of the City University of New York, New York, NY (US)

(72) Inventors: Hiroshi Matsui, New York, NY (US); Roberto de la Rica, New York, NY (US); Menglu Shi, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 293 days.

(21) Appl. No.: 13/887,587

(22) Filed: May 6, 2013

(65) Prior Publication Data

US 2014/0326071 A1 Nov. 6, 2014

(51) Int. Cl.
*G01B 7/16* (2006.01)
*G01L 1/00* (2006.01)
*G01L 7/08* (2006.01)
*G01N 33/574* (2006.01)
*C12N 15/82* (2006.01)

(52) U.S. Cl.
CPC .......... *G01N 33/574* (2013.01); *C12N 15/8216* (2013.01)

(58) Field of Classification Search
None
See application file for complete search history.

(56) References Cited

U.S. PATENT DOCUMENTS

| | | | |
|---|---|---|---|
| 6,800,649 B1 * | 10/2004 | Uckun | 514/345 |
| 7,622,271 B2 * | 11/2009 | Kennedy et al. | 435/7.31 |
| 2003/0042150 A1 * | 3/2003 | Ryu et al. | 205/778 |
| 2004/0023253 A1 * | 2/2004 | Kunwar et al. | 435/6 |
| 2005/0084865 A1 * | 4/2005 | Yu et al. | 435/6 |
| 2005/0142033 A1 * | 6/2005 | Glezer et al. | 422/58 |
| 2006/0099578 A1 * | 5/2006 | Wallace et al. | 435/6 |
| 2010/0193378 A1 | 8/2010 | Bratov et al. | |
| 2013/0059783 A1 * | 3/2013 | Flygare et al. | 514/13.5 |

\* cited by examiner

*Primary Examiner* — Peter Macchiarolo
*Assistant Examiner* — Jermaine Jenkins
(74) *Attorney, Agent, or Firm* — Peter J. Mikesell; Schmeiser, Olsen & Watts, LLP

(57) ABSTRACT

The subject matter disclosed in this specification pertains to a method for detecting cells with elastic cell membranes. A plurality of cells are fixed to an impedimetric transducer and osmotic stress is applied. Those cells with elastic membranes, including cancer cells, undergo a volume change which is detected by the impedimetric transducer.

19 Claims, 5 Drawing Sheets

METHOD FOR DETECTING CELLS WITH ELASTIC CELL MEMBRANES

STATEMENT OF FEDERALLY SPONSORED RESEARCH OR DEVELOPMENT (IF NECESSARY)

This invention was made with Government support under grant number ECCS-082390 awarded by the Natural Science Foundation (NSF). The government has certain rights in the invention.

BACKGROUND OF THE INVENTION

The subject matter disclosed herein relates to method for detecting cancerous cells. Detection and assay of cancer cells are normally pursued by labeling the cells with biomarkers. However, biomarkers for specific cancers vary dependent on patients, races, health history, and the like. There are no universal biomarkers available for the diagnostics. Another current limitation on cancer cell detection is to target cancer cells in different aggressiveness. There are no specific biomarkers to screen the grade of cancer cells and many times positive diagnostics appears even though cancers are low grade and low risk. It would therefore be desirable to provide an alternative method for detecting cancerous cells that address at least some of these shortcomings.

The discussion above is merely provided for general background information and is not intended to be used as an aid in determining the scope of the claimed subject matter.

BRIEF DESCRIPTION OF THE INVENTION

In one embodiment, a method for detecting cells with elastic cell membranes is disclosed. The method comprising the steps of fixing a plurality of cells to an impedimetric transducer; applying osmotic stress to the plurality of cells; waiting for a predetermined time to permit the plurality of cells to change in volume due to the osmotic stress; and detecting the change in volume with the impedimetric transducer and determining cells with elastic cell membranes are present in the plurality of cells.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 3A depicts the percent variation of the diameter of K:Molv NIH 3T3 cancel cells while

DETAILED DESCRIPTION OF THE INVENTION

A method for detecting cells with elastic cell membranes is described herein. Without wishing to be bound to any particular theory, it is believed the mechanoelastic properties of the cell members of cancer cells are substantially softer (e.g. 70% for breast cancer cells) than normal cells. This change may be due to structural changes in the membrane, cytoskeleton and cell brush as normal cells turn to cancer cells. To detect the mechanical property change of cells with more simplified procedure, reduced time, and higher throughput, osmotic stress is applied to cancer cells in method 100 to observe the rapid volume change of softer cancel cells induced by this internal pressure change. Cancer cells were observed to swell while normal cells the volume of normal cells is constant. In one embodiment, the osmotic pressure is hyposmotic pressure which induces swelling in cancer cells. The swelling behavior can be applied as a diagnostic fingerprint to selectively detect cancer cells. The technique has shown a detection limit of less than five cells per milliliter within thirty minutes. The technique requires no biomarkers and no complex washing or separation processes.

Figure 1:
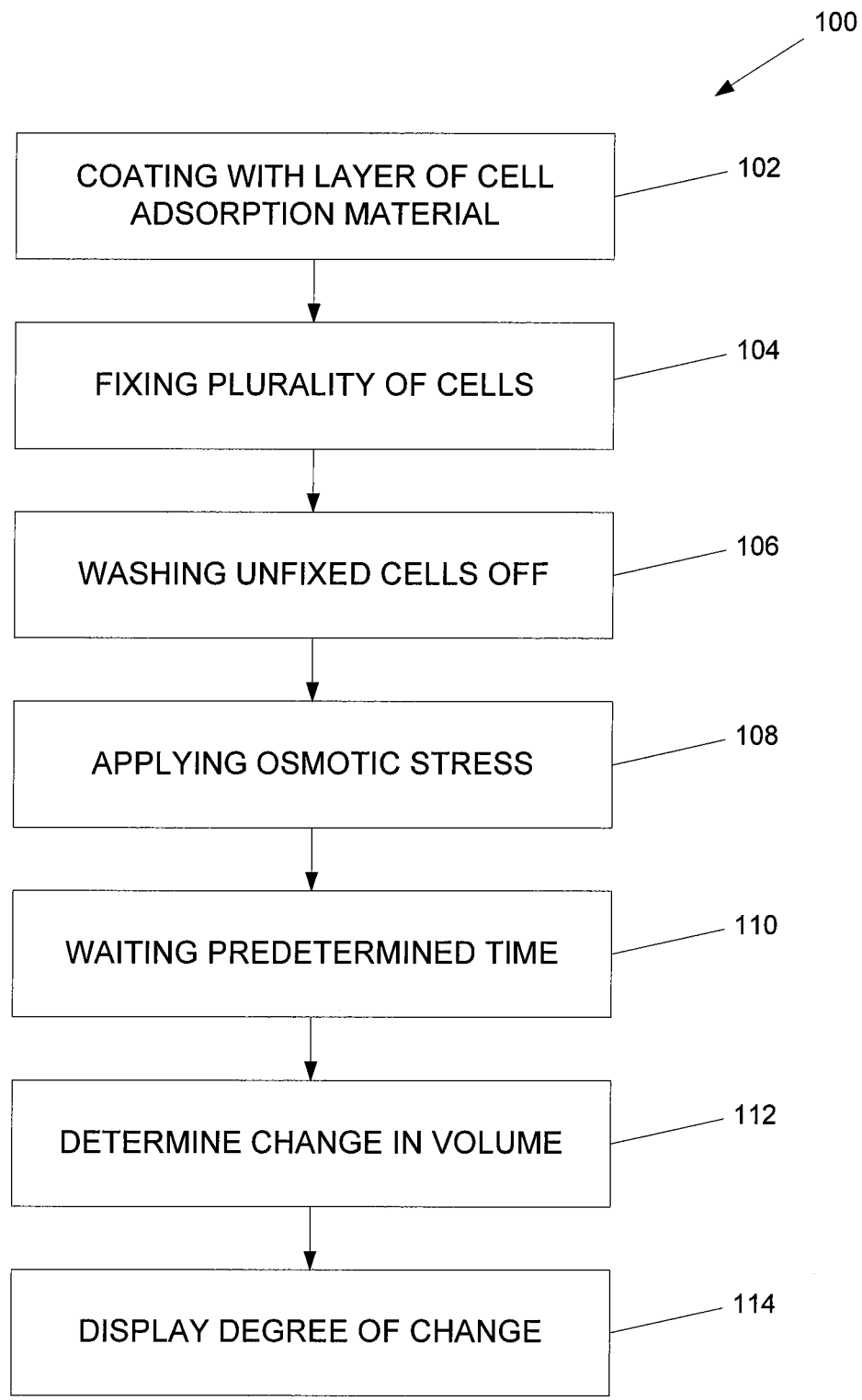
FIG. 1 is a flow diagram of an exemplary method for detecting cells with elastic cell membranes.
Figure 2:
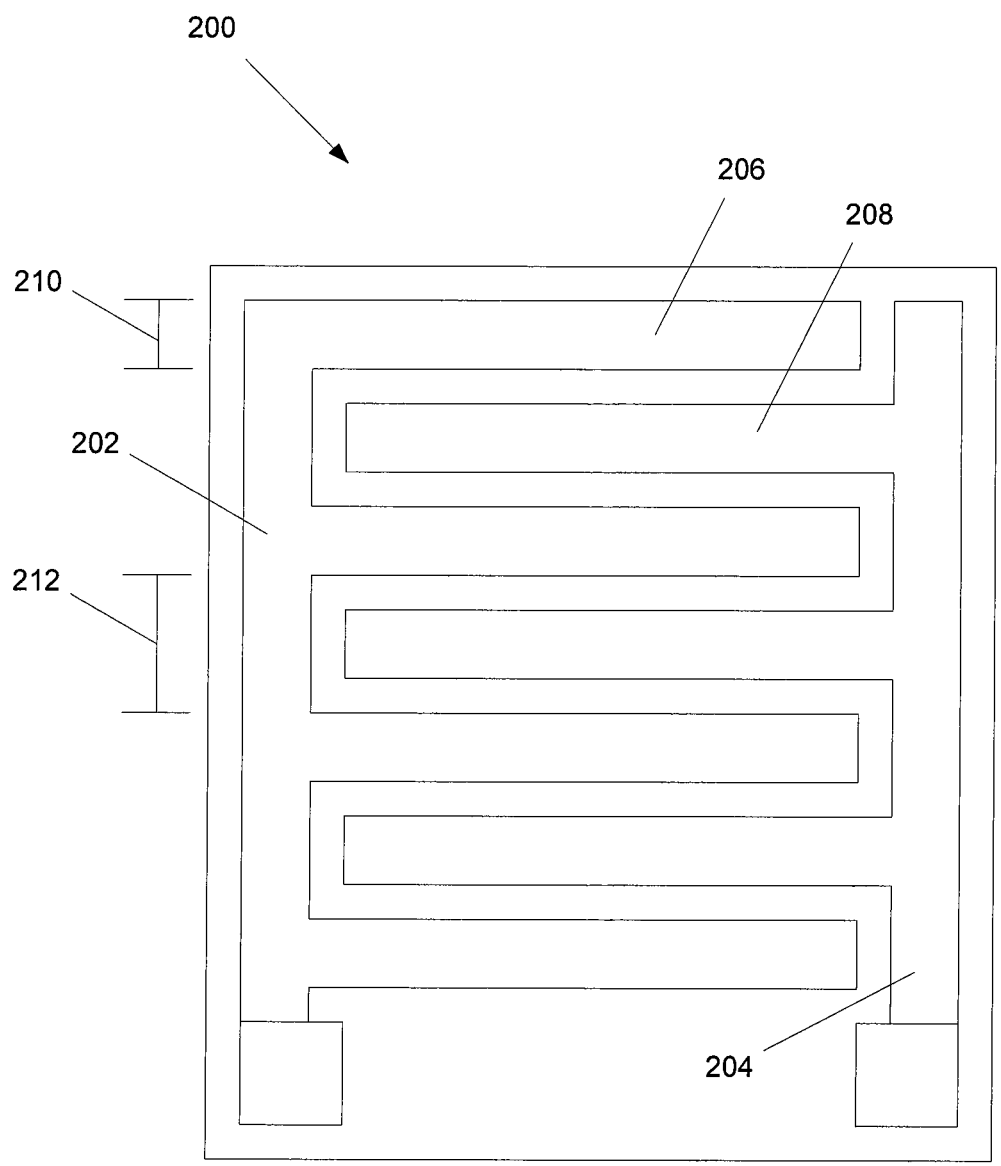
FIG. 2 is a top view of the exemplary impedimetric transducer for cancer cell detection platform.

FIG. 1 depicts a method 100 for detecting cells with elastic cell membranes. The method 100 may use an impedimetric transducer such as the impedimetric transducer 200 of FIG. 2. FIG. 2 is a top view of the exemplary impedimetric transducer 200. The underlying chip may be a polysilicon sensor chip. The impedimetric transducer 200 comprises a pair of interdigitated electrodes, 202, 204, each comprising a plurality of digits 206, 208. The digits 206, 208 each have a width 210. In one embodiment, the width 210 is about three micrometers. The interdigitated electrodes 202, 204 have a pitch 212. In one embodiment, the pitch 212 is about six micrometers.

In step 102 of method 100, an impedimetric transducer is coated with a layer of cell adsorption material. In one embodiment, the cell adsorption material is selected from the group consisting of polylysine and fibronectin. For example fifty micrometers of a cell adsorption material (one mg per ml) may be deposited on the impedimetric transducer for sixty minutes.

After the cell adsorption material is coated on the impedimetric transducer 200, a sample comprising a plurality of cells is contacted with the impedimetric transducer 200. In one embodiment, the sample is a whole cell liquid sample, such as a urine or blood sample. In another embodiment, the sample is a processed sample, such as a centrifuged or filtered sample. In one exemplary embodiment, a five microliter sample is used. In step 104, at least some of the cells in the plurality of cells are fixed to the impedimetric transducer 200. For example, the sample may be contacted with the impedimetric transducer 200 for thirty minutes to permit the step of fixing to occur.

Thereafter, in step 106, unfixed cells are washed off of the impedimetric transducer 200. For example, the impedimetric transducer 200 may be dipped quickly into water several times (e.g. three) to remove unwanted material.

In step 108, osmotic stress is applied to the plurality of cells. In one embodiment, the osmotic stress is hyposmotic stress. Such a stress may be applied, for example, by treating the plurality of cells with 100 microliters of deionized water. In another embodiment, the osmotic stress is hyperosmotic stress. Such a stress may be applied, for example, by treating the plurality of cells with 100 microliters of a solution with relatively high salt concentration.

Figure 3A:
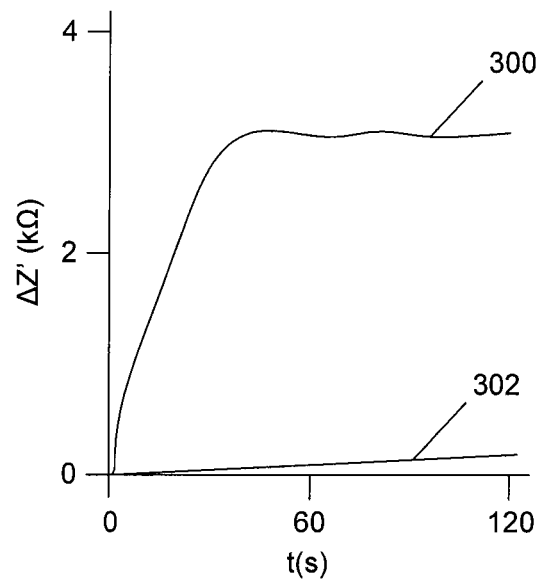
Figure 3B:
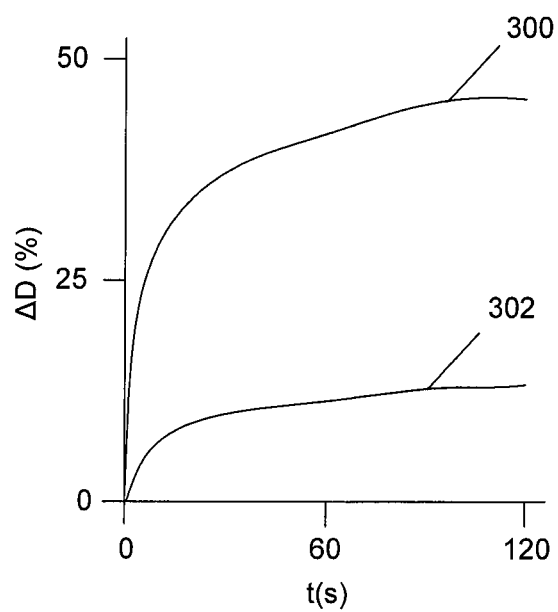
FIG. 3B shows the variation of the real part of the impedance under hyposmotic pressure.

In step 110, a predetermined amount of time is permitted to pass while the plurality of cells react to the osmotic stress. As shown in FIGS. 3A and 3B, cancerous and non-cancerous cells respond rapidly to the osmotic stress.

FIG. 3A depicts the percent variation of the diameter of K:Molv NIH 3T3 cancel cells (300) and NIH 3T3 normal cells (302) as determined by optical imaging. The cancerous cells clearly show a rapid change in diameter within the first minute. In stark contrast, the normal cells show comparatively no change in diameter over the same time period. FIG. 3B shows the variation of the real part of the impedance (Z') at 20 kHz under the same conditions. The results of the impedance graph (FIG. 3B) parallel the results of the optical imaging graph (FIG. 3A) showing a clear correlation. The normal cells showed cytoplasm extruding outward through breaking points of membranes but the overall cell size is essentially maintained. Accordingly, in FIG. 3B, the impedance of normal cells 302 remained substantially constant. In contrast, the cancerous cells 300 showed a substantial change in their diameter which resulted in a corresponding change in the impedance value for that sample.

In step 112, after a predetermined amount of time has been permitted to pass, a change in the volume of at least some of the cells in the plurality of cells is detected by the impedimetric transducer 200 as a result of a change in impedance. In one embodiment, an impedance value is recorded after a predetermined period of time has passed. In another embodiment, the impedance value is monitored throughout the predetermined period of time to detect the rate of change (e.g. slope) of the impedance value. Zero or a modest level of change indicates normal cells. A more rapid rate of change indicates cancerous cells.

In step 114 the degree of change in volume is displayed to a user. For example, a change in impedance values between two time periods may be displayed showing starting impedance and ending impedance after, for example, two minutes. In another embodiment, the rate of change in impedance values as a function of time between the two time periods is displayed.

Figure 4A:
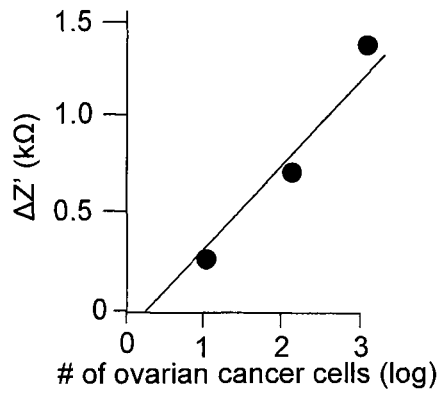
FIG. 4A, FIG. 4B, FIG. 4C and FIG. 4D are graphs that correlate the number of cancerous cells deposited to level of impedance after two minutes.
Figure 4B:
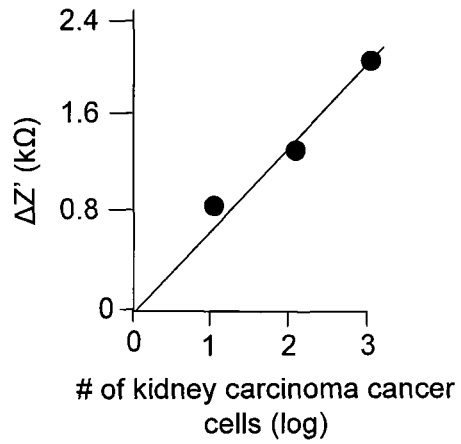
Figure 4C:
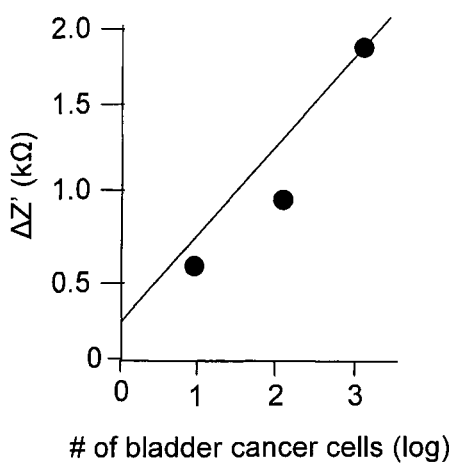
Figure 4D:
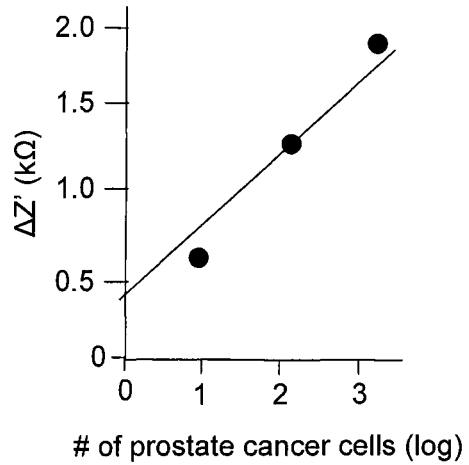

With reference to FIG. 4A to FIG. 4D, four exemplary samples are show that correlate number of cancerous cells deposited to level of impedance after two minutes. FIG. 4A shows the variation in impedance after two minutes with samples having different levels of ovarian cancer cells (x-axis) in $10^3$ OSE cells (non-cancer cells). FIG. 4B shows a corresponding graph showing impedance after two minutes of samples having different levels of kidney carcinoma cells in $10^3$ HEK293 cells (non-cancer cells). FIG. 4C shows a corresponding graph showing impedance after two minutes of samples having different levels of HT-1197 bladder cancer cells in urine containing $10^3$ RT4 cells (non-cancer cells). FIG. 4D shows a corresponding graph showing impedance after two minutes of samples having different levels of PC3 prostate cancer cells in urine containing $10^3$ PNT1a cells (non-cancer cells).

Figure 5A:
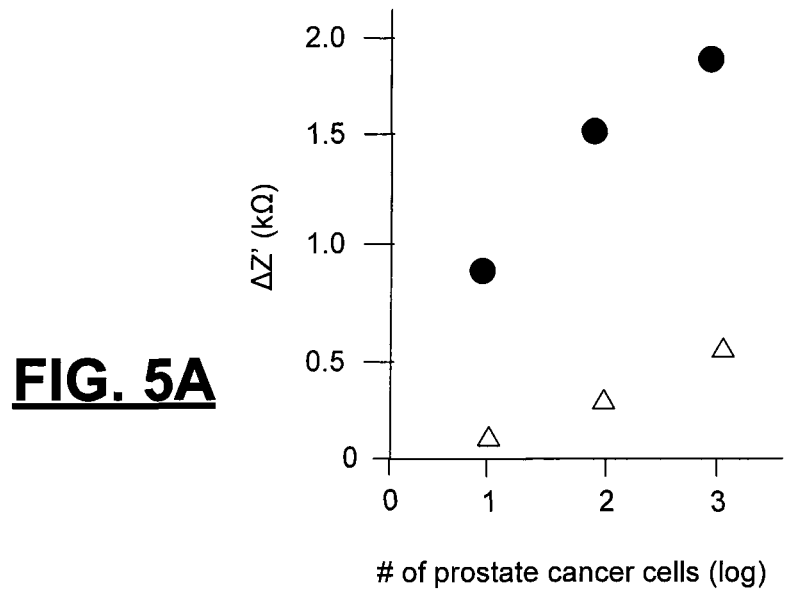
FIG. 5A and FIG. 5B are graphs that correlate the grade of cancer cells deposited to level of impedance after two minutes.
Figure 5B:
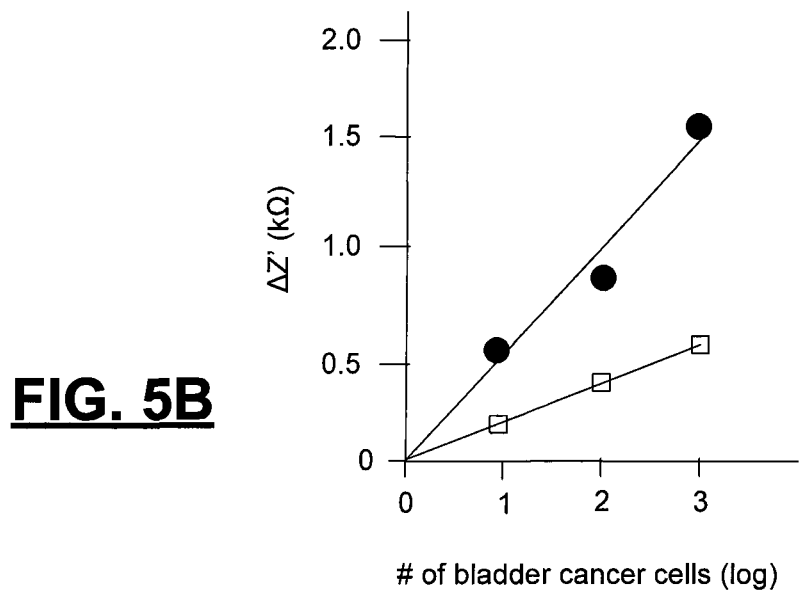

Referring to FIG. 5A and FIG. 5B, the graphs illustrate the application of the disclosed method to determine not only the presence, but also the grade of, the cancer cell. In FIG. 5A line 500 depicts PC-3 prostate cancer cells (grade 4) while line 502 depicts DU-145 prostate cancer cells (grade 2). The impedance values of grade 4 cancer cells showed a greater change after two minutes than those of grade 2 cancer cells. Likewise, in FIG. 5B, TCCSUP bladder cancer cells (grade 4) showed a greater change after two minutes than those of HT5637 bladder cancer cells (grade 2).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for detecting cells with elastic cell membranes, the method comprising the steps of:
   fixing a plurality of cells to an impedimetric transducer;
   applying osmotic stress to the plurality of cells;
   waiting for a predetermined time to permit the plurality of cells to change in volume due to the osmotic stress;
   detecting the change in volume with the impedimetric transducer and determining cells with elastic cell membranes are present in the plurality of cells.

2. The method as recited in claim 1, wherein the impedimetric transducer comprises interdigitated electrodes.

3. The method as recited in claim 2, wherein the interdigitated electrodes each comprise a digit with a width of about three to ten micrometers.

4. The method as recited in claim 2, wherein the interdigitated electrodes have a pitch of about three to ten micrometers.

5. The method as recited in claim 2, wherein the impedimetric transducer is coated with a layer of cell adsorption material.

6. The method as recited in claim 5, further comprising fixing the plurality of cells to the layer of cell adsorption material prior to the step of applying osmotic stress.

7. The method as recited in claim 6, further comprising washing unfixed cells off of the impedimetric transducer, the step of washing unfixed cells being performed after the step of permitting the plurality of cells to become fixed to the layer of cell adsorption material and prior to the step of applying osmotic stress.

8. The method as recited in claim 5, wherein the adsorption material is selected from the group consisting of polylysine and fibronectin.

9. The method as recited in claim 1, wherein the predetermined time is at least about one minute.

10. The method as recited in claim 1, wherein the predetermined time is from about one minute to about two minutes.

11. A method for detecting cells with elastic cell membranes, the method comprising the steps of:
- fixing a plurality of cells to an impedimetric transducer;
- applying hyposmotic stress to the plurality of cells;
- waiting for a predetermined time to permit the plurality of cells to change in volume due to the hyposmotic stress;
- detecting an increase in volume with the impedimetric transducer and determining cells with elastic cell membranes are present in the plurality of cells; and
- displaying the degree of increase in volume to a user.

12. The method as recited in claim 11, wherein the interdigitated electrodes each comprise a digit with a width of about three to ten micrometers.

13. The method as recited in claim 11, wherein the interdigitated electrodes have a pitch of about three to ten micrometers.

14. The method as recited in claim 11, wherein the impedimetric transducer is coated with a layer of cell adsorption material.

15. The method as recited in claim 14, further comprising fixing the plurality of cells to the layer of cell adsorption material prior to the step of applying osmotic stress.

16. The method as recited in claim 15, further comprising washing unfixed cells off of the impedimetric transducer, the step of washing unfixed cells being performed after the step of permitting the plurality of cells to become fixed to the layer of cell adsorption material and prior to the step of applying osmotic stress.

17. The method as recited in claim 15, wherein the adsorption material is selected from the group consisting of polylysine and fibronectin.

18. The method as recited in claim 11, wherein the predetermined time is at least about one minute.

19. The method as recited in claim 11, wherein the predetermined time is from about one minute to about two minutes.

* * * * *